United States Patent [19]

Shih et al.

[11] Patent Number: 4,918,204

[45] Date of Patent: Apr. 17, 1990

[54] TETRAHYDROFURAN PURIFICATION

[75] Inventors: T. Thomas Shih, Bryn Mawr; Te Chang, West Chester, both of Pa.

[73] Assignee: Arco Chemical Technology, Inc., Wilmington, Del.

[21] Appl. No.: 303,325

[22] Filed: Jan. 30, 1989

[51] Int. Cl.$^4$ ............................................. C07D 307/08
[52] U.S. Cl. .................................... 549/429; 549/509
[58] Field of Search ................................ 549/429, 509

[56] References Cited

U.S. PATENT DOCUMENTS 4,093,633  2/1978  Tanabe et al. ................. 260/346.11
4,665,205  5/1987  Yamada et al. ...................... 549/509

Primary Examiner—Richard L. Raymond
Attorney, Agent, or Firm—Lewis J. Young

[57] ABSTRACT

Purification of tetrahydrofuran from the dehydrocyclization of 1,4-butanediol in the presence of an organic acid catalyst has been accomplished by the extractive distillation of crude tetrahydrofuran containing water using monopropylene glycol as an extractive solvent.

3 Claims, No Drawings

TETRAHYDROFURAN PURIFICATION

BACKGROUND OF THE INVENTION

This invention relates to the purification of crude tetrahydrofuran prepared by the dehydrocyclization of 1,4-butandiol in the presence of an organic acid catalyst. The tetrahydrofuran, which forms an azeotropic mixture with water, is separated and purified to a high quality in a high yield by extractive distillation of the crude mixture.

Tetrahydrofuran (THF) has been widely used in various fields as a solvent for various organic compounds or high polymers and also as an intermediate of various organic compounds. Recently, THF has further found its use as a starting material or an auxiliary for synthetic polymers in textiles and plastics.

A number of methods have previously been suggested for the separation of THF from its water azeotrope. These generally consist of methods such as adding glycerine to a THF azeotrope whereby a layer separation occurs in which there is a THF-water layer containing more THF than the azeotrope which then can be distilled to yield anhydrous THF. The bottom layer contains more water than the azeotrope and can be concentrated to the azeotrope again by distillation. The use of a hydrocarbon, such as toluene or halo or nitro hydrocarbon of boiling point higher than THF has been disclosed for extraction.

Other methods of drying such materials were suggested, as adding a drying agent such as silica gel or calcium chloride or alumina or molecular sieves to the material to remove water. It is also known from U.S. Pat. No. 4,093,633 to produce anhydrous THF from its azeotropic mixtures by subjecting the mixtures to a two-step continuous distillation under two different pressures. U.S. Pat. No. 4,665,205 teaches that in the production of THF from 1,4-butanediol, 1,4-butanediol can be used as the extractive solvent to remove water from the reaction product and yield anhydrous THF.

BRIEF SUMMARY OF THE INVENTION

We have now found that the addition of certain 1,2-glycols as an extractive solvent can lead to the recovery of high purity THF from its water mixtures by extractive distillation of the product of dehydrocyclization of 1,4-butanediol.

DETAILED DESCRIPTION OF THE INVENTION

The initial dehydrocyclization reaction occurs in a reaction column which contains a catalyst such as sulfuric acid or a cation exchange resin. To the column is added 1,4-butanediol and the temperature of the reactor is maintained at 60° to 200° C. and the pressure is maintained between 1 and 10 Kg/cm$^2$.

From the top of the reactor column is obtained a mixture of tetrahydrofuran, impurities such as 2,3-dihydrofuran, and water which is led to an extractive distillation column. To this mixture in the column is added a 1,2-glycol to act as an extractive solvent. The 1,2-glycol may be especially ethylene glycol or monopropylene glycol. The extractive distillation column may be of a conventional type and is not limited critically. This column may have from 30 to 60 theoretical trays, and will be operated at solvent to feed ratios between 0.25 and 9.0 with a preferred range of between 1.0 and 4.0. The normal operating temperatures will be between 40° and 200° C., preferably between 60° and 150° C., at a reflux ratio of from 0.05 to 5.0, preferably from 0.2 to 1.0. The usual pressures will vary between 5 and 190 psia with a preferred range between 10 and 50 psia.

The overhead stream from the extractive distillation column is fed to a Lights Removal Column where the purified tetrahydrofuran is removed as bottoms material and the light impurities such as the 2,3-dihydrofuran is removed as overhead. The Lights Removal Column should contain from 10 to 40 theoretical trays which are operated at a reflux ratio of 0.5–5.5, preferably 1.0–3.0, at a temperature of 40°–150° C., preferably 50°–100° C. and at a pressure of 5–120 psia, preferably 10–40 psia.

The bottoms stream from the extractive distillation column is fed to a Solvent Stripper column where all the impurities are stripped out with water in overhead and the lean glycol solvent was recovered from the bottoms and recycled to the extractive distillation column. The Stripper Column will have from 10 to 30 theoretical trays which are operated at a reflux ratio of 0.05–3.0, preferably 0.1–1.0, at a temperature of 40°–230° C., preferably 40°–190° C., and at a pressure of 1–50 psia, preferably 1–15 psia.

Another advantage of this invention is that the extractive column removes all the heavy impurities during water removal. No additional heavies column is required compared to a conventional distillation.

The invention is further illustrated but not limited by the example.

EXAMPLE I

A series of continuous distillations were performed in a one-inch Oldershaw unit which consisted of three columns in sequence—Extractive distillation, Stripper, and Lights Removal columns with 42, 15, and 15 theoretical stages, respectively. About 183 g/hr of crude THF containing primary water (20 wt %), 200 ppm of 2,3-dihydrofuran (a light key component), and a total of 3000 ppm of heavy impurities was fed to the 32nd stage (from the top) of the Extractive Column, while the monopropylene glycol solvent was fed to the 10th stage at a rate of 241 g/hr (a solvent to feed ratio of 1.32). The column was operated at atmospheric pressure with a reflux ratio of 1. The corresponding temperatures were 65° C., and 145° C. at the top and bottoms of the column, respectively. About 135 g/hr of THF which contained only 140 ppm of water and 300 ppm of 2,3-dihydrofuran was taken overhead and fed to the Lights Removal Column (8th stage from the top). No heavy key component of methyl THF was detected in this overhead THF.

The overhead stream of the Extractive Column was fed to the 8th stage of the Lights Removal Column (135 g/hr) which was operated at atmospheric pressure (a bottoms temperature of 66° C.) and with a reflux ratio of 1.4. About 133 g/hr of high purity THF product was recovered as the bottom product. This THF product contained 40 ppm water, 30 ppm of 2,3-dihydrofuran and 40 ppm of other heavy impurities.

The bottoms stream of the Extractive Column (289 g/hr) was sent to the Solvent Stripper (at the 8th stage from the top) where all the impurities were stripped out with water in overhead and about 242 g/hr of lean glycol solvent was recovered from the bottoms and recycled to the Extractive Column. The Stripper Column was also operated at atmospheric pressure with a bottoms temperature of 190° C. and a reflux ratio of 1.

EXAMPLE II

Comparative Example (Not this Invention)

About 366 g/hr of crude THF having the same composition as that used in Example I was fed to a 40-tray (15 theoretical) one-inch Oldershaw distillation column at 21st tray from the top. The column was operated at atmospheric pressure with a reflux ratio of 1.7. The corresponding temperatures were 63° and 102° C. at the top and bottom of the column, respectively. About 304 g/hr of THF/water azeotrope mixture was recovered overhead. This mixture contained 94.1% THF, 5.7% water, 0.2% methyl THF, 100 ppm dimethyl THF and 230 ppm 2,3-dihydrofuran. The heavy key component of methyl THF had not been removed at all. Additional heavies column was required in this conventional scheme to produce a similar quality THF product to that made by the extractive distillation with no additional heavies column.

We claim:

1. A process for recovering tetrahydrofuran in pure form from a water azeotrope formed during the dehydration of 1,4-butanediol in the presence of an acid catalyst consisting of contacting said azeotrope with an appropriate 1,2-glycol in an extractive distillation column.

2. The process of claim 1 wherein said appropriate glycol is ethylene glycol.

3. The process of claim 1 wherein said appropriate glycol is monopropylene glycol.

* * * * *